United States Patent
Bannerman et al.

(10) Patent No.: US 11,485,962 B2
(45) Date of Patent: Nov. 1, 2022

(54) RHODOCOCCUS RHODOCHROUS STRAIN AND USE THEREOF IN THE PRODUCTION OF ACRYLIC ACID

(71) Applicant: AECI LIMITED, Sandton (ZA)

(72) Inventors: Natasha Bannerman, Sandton (ZA); Nolusizo Khaliphile Dlalisa, Sandton (ZA); Lee Anne Etty, Sandton (ZA)

(73) Assignee: AECI LIMITED, Sandton (ZA)

( * ) Notice: Subject to any disclaimer, the term of this patent is extended or adjusted under 35 U.S.C. 154(b) by 26 days.

(21) Appl. No.: 17/268,561

(22) PCT Filed: Aug. 16, 2019

(86) PCT No.: PCT/ZA2019/050047
§ 371 (c)(1),
(2) Date: Feb. 15, 2021

(87) PCT Pub. No.: WO2020/037338
PCT Pub. Date: Feb. 20, 2020

(65) Prior Publication Data
US 2021/0340517 A1    Nov. 4, 2021

(30) Foreign Application Priority Data
Aug. 16, 2018   (ZA) ................................ 2018/05469

(51) Int. Cl.
*C12N 9/78* (2006.01)
*C12P 7/40* (2006.01)

(52) U.S. Cl.
CPC .................. *C12N 9/78* (2013.01); *C12P 7/40* (2013.01); *C12Y 305/05001* (2013.01)

(58) Field of Classification Search
CPC ..................................... C12N 9/78; C12P 7/40
See application file for complete search history.

(56) References Cited

U.S. PATENT DOCUMENTS 5,998,180 A    12/1999 Armitage et al.

FOREIGN PATENT DOCUMENTS

CN    105420154 A    3/2016

OTHER PUBLICATIONS

International Search Report and Written Opinion for Application No. PCT/ZA2019/050047 dated Nov. 6, 2019 (13 pages).
Sankhian et al., "Nitrile hydratase of Rhodococcus rhodochrous NHB-2: Optimisation of conditions for production of enzyme and conversion of acrylonitrile to acrylamide," Asian Jr. of Microbiol Biotech Env. Sc., 2003, 5(2):217-223.
Kobayashi et al., "Purification and characterization of a novel nitrilase of Rhodococcus rhodochrous K22 that acts on aliphatic nitriles," J. Bacteriol., 1990, 172(9):4807-15.
Nagasawa et al., "ε-caprolactam, a new powerful inducer for the formation of Rhodococcus rhodochrous J1 nitrilase," Arch. Microbiol., 1990, 155(1):13-17.

*Primary Examiner* — Yong D Pak
(74) *Attorney, Agent, or Firm* — Michael Best & Friedrich LLP

(57) ABSTRACT

A strain of *Rhodococcus rhodochrous* in which a gene coding at least part of a nitrile hydratase enzyme or any gene coding a protein involved in the transcription, translation or formation of at least part of the nitrile hydratase enzyme has been deactivated or rendered ineffective or a strain of *Rhodococcus rhodochrous* cultured under condition wherein the nitrile hydratase enzyme is been inhibited.

8 Claims, No Drawings

RHODOCOCCUS RHODOCHROUS STRAIN AND USE THEREOF IN THE PRODUCTION OF ACRYLIC ACID

CROSS REFERENCE TO RELATED APPLICATIONS

This application is a U.S. National Phase application under 35 U.S.C. § 371 from International Patent Application No. PCT/ZA2019/050047 filed Aug. 16, 2019, which claims priority to South African Patent Application No. 2018/05469 filed on Aug. 16, 2018, the contents of each of which are incorporated by reference herein in its entirety.

BACKGROUND OF THE INVENTION

This invention relates to a microorganism capable of producing an enzyme to convert acrylonitrile to acrylic acid and to a method of culturing the microorganism.

Acrylic acid is an important starting material in the synthesis of a diverse range of polymers used in applications such as the production of paper, the production of potable water, in mining, and in the treatment of sewerage.

Traditionally acrylic acid is manufactured through gas-phase oxidation of propylene with the use of a chemical catalyst at high temperatures. This chemical conversion process is not selective and can result in a number of impurities being formed due to uncontrolled side reactions. Another drawback of a chemical catalysis process is the difficulty of subsequently recovering the catalyst and the purification of the final product which requires energy intensive distillation. For this reason, the application of a biocatalyst is considered an attractive option.

The applicant is aware of two processes for producing acrylic acid via direct fermentation using microorganisms.

A first fermentation process makes use of a renewable carbon source and produces lactic acid, 3-hydroxypropionic acid and glycerol. The process is carried out using naturally occurring microorganisms. The resulting product requires further processing (typically using engineered microorganisms) to produce acrylic acid.

A biosynthetic pathway suggested by Chu, et al., 2015 was designed for the production of acrylic acid from glucose. Use is made of a genetically engineered strain of *Escherichia coli* to produce 3-hydroxypropionic acid and then acrylic acid from glucose fermentation. The fermentation of glucose to 3-hydroxypropionic acid is followed by three enzymatic steps to produce an acrylic acid and CoA combination from which acrylic acid can be extracted.

A drawback of direct fermentation of glucose for the production of acrylic acid via a 3-hydroxypropionic acid route is that a very low acrylic acid titer is produced (0.12 g/L). This is due to the acrylic acid product being toxic to the microorganism and thus, after a low level of product has been produced, the microorganism is killed/deactivated A second strategy (using a non-carbon-based source) is based on a biosynthetic pathway which employs a nitrilase to convert acrylonitrile to acrylic acid and ammonium acrylate. Nitrilases are enzymes available in mostly soil-inhabiting microorganisms like *Rhodococcus rhodochrous*.

In a study by Armitage, et al., 1999, *Rhodococcus rhodochrous* NCIMB 40757 or NCIMB 40833 was used to convert acrylonitrile to ammonium acrylate in aqueous solutions or vapour. These organisms use two separate metabolic pathways concurrently to produce acrylic acid from acrylonitrile. The first pathway relies on the microorganism's production of nitrilase to convert the substrate (acrylonitrile) directly into acrylic acid. The second pathway relies on the microorganism's production of nitrile hydratase and amidase to produced acrylic acid in a two-step process in which the acrylonitrile is converted to acrylamide (unwanted intermediate) by nitrile hydratase and the subsequently the acrylamide is converted to acrylic acid by amidase. Typically, this process produces a final ammonium acrylate product at a concentration of about 5.68 M after a reaction time of 6.7 hours with a residual acrylamide concentration of 0.023 M. In organisms where amidase is defective and nitrile hydratase is active, the acrylic acid product will be contaminated with acrylamide.

Another drawback of the use of the aforementioned organisms is that the nitrilase enzyme is inhibited at high concentrations of the substrate acrylonitrile and can only metabolise the substrate at concentrations between 125 mM and 17 5 mM.

It is an aim of the current invention to provide an organism which is capable of producing acrylic acid from an acrylonitrile substrate using a single metabolic pathway that is reliant on a single enzyme, and to provide a method of cultivating such an organism.

SUMMARY OF THE INVENTION

In a biochemically catalysed process, energy efficiency can be increased by reducing the number of enzymes required to convert a substrate into an end product. Thus a strategy to reduce unwanted intermediate products, as well as the enzymes needed to eliminate these intermediate products, is required.

The invention provides a strain of *Rhodococcus rhodochrous* wherein:
1. at least a part of a gene coding at least a part of a nitrile hydratase enzyme has been deactivated or rendered ineffective; or
2. any related gene coding a protein involved in the transcription, translation or formation at least part of the nitrile hydratase enzyme has been deactivated or rendered ineffective.

The aforementioned genes may hereinafter be referred to as undesired genes.

The genes coding for the nitrile hydratase enzyme and the undesired genes may be deactivated or rendered inefficient by means of any suitable optimization process. The optimization process may include artificial selection processes as well as gene knock-out or knock-in processes The invention also provides a strain of *Rhodococcus rhodochrous* in which the nitrile hydratase enzyme has been inhibited.

Any component of the nitrile hydratase enzyme or any other protein necessary for the functioning or formation of the nitrile hydratase enzyme, or any other protein necessary for the effective transcription or translation of the gene coding for nitrile hydratase may be inhibited.

The nitrile hydratase enzyme and any of the other related proteins may be inhibited by the addition of a suitable inhibitor during culturing of the strain. The inhibitor for inhibiting the nitrile hydratase enzyme may be isobutyronitrile.

The invention further extends to a strain of *Rhodococcus rhodochrous* in which the nitrilase enzyme has been induced.

The nitrilase enzyme may be induced by the addition of a suitable inducer during culturing of the strain. The inducer may be ε-caprolactam.

The invention further extends to a naturally adapted strain of *Rhodococcus rhodochrous* which has been adapted to produce a nitrilase enzyme that is active at a high concentration of acrylonitrile. The concentration of acrylonitrile may be above 175 mM.

The adapted strain may be optimised by artificially selecting individuals, from the strain, which individuals have shown nitrilase activity at concentrations above 175 mM and further culturing the selected individuals.

The selected individuals from the naturally adapted strain may be subjected to a gene knock-out process during which one or more of the undesired genes are replaced with a defective or mutated version of the gene. One example of an undesired gene is nitrile hydratase.

The invention further extends to a strain of *Rhodococcus rhodochrous*, or any modification or mutant thereof, deposited in terms of the Budapest Treaty on 11 Sep. 2017 under accession number NCIMB 42803 at NCIMB Ltd, an international Depository Authority situated at Bucksburn, Aberdeen, AB21 9YA, Scotland. The deposit will be maintained at the NCIMB depository under the terms of the Budapest Treaty on the International Recognition of the Deposit of Microorganisms for the Purposes of Patent Procedure for a term of at least thirty years and at least five years after the most recent request for the furnishing of a sample of the deposit was received by the depository. Applicants have satisfied and will comply with the requirements of 37 C.F.R. §§ 1.801-1.809. Additional deposits will be made at the NCIMB as needed to ensure availability. Applicants impose no restrictions on the availability of the deposited material from the NCIMB after the issuance of a patent from this application.

The strain of *Rhodococcus rhodochrous* NCIMB 42803 or a modification or mutant thereof may have at least a part of a gene coding at least a part of a nitrile hydratase enzyme that has been deactivated or rendered ineffective.

The strain of *Rhodococcus rhodochrous* NCIMB 42803 or a modification or mutant thereof may have any gene coding for a protein involved in the transcription, translation or formation of at least part of the nitrile hydratase enzyme that has been deactivated or rendered ineffective.

The strain of *Rhodococcus rhodochrous* NCIMB 42803 or a modification or mutant thereof may have been optimised to express a nitrilase enzyme which is not deactivated at concentrations of acrylonitrile exceeding 175 mM.

The strain of *Rhodococcus rhodochrous* NCIMB 42803 or a modification or mutant thereof may be cultivated in the presence of isobutyronitrile to inhibit residual nitrile hydratase activity.

The strain of *Rhodococcus rhodochrous* NCIMB 42803 or a modification or mutant thereof may be cultivated in the presence of be ε-caprolactam to induce production of nitrilase

DETAILED DESCRIPTION

A strain of *Rhodococcus rhodochrous* identified as NCIMB 42803 is cultivated in a growth medium, (containing g/L to 6 g/L ε-caprolactam) at 30° C. to 40° C. for 120 hours (5 days) in 300 mL conical flask. Inhibition of nitrile hydratase produced by the *Rhodococcus rhodochrous* strain is achieved by adding 2 g/L to 10 g/L of isobutyronitrile. The process is up-scaled to a 3 L volume in a Sarorius 5 L glass bioreactor for a larger yield of enzyme and cell production for use in a bioconversion application.

Bioreactions are performed in a bioreactor at 1 L volumes in which acrylonitrile is added to a reactor containing water and a required quantity of biomass with enzyme activity of 900 000-1 000 000 U/L. Acrylonitrile is added at a slow rate to keep the acrylonitrile level below toxic levels and to avoid polymerisation. A reaction that takes place in the reactor is as follows:

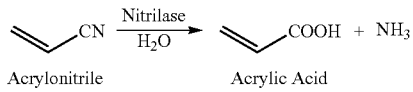

Acrylonitrile → Acrylic Acid

In one example (as shown in the reaction above) the acrylic acid, produced during the biocatalyzed process of the invention, is combined with ammonia ($NH_3$) which reacts in-situ with the acrylic acid ($C_3H_4O_2$) to produce an ammonium acrylate ($C_3H_7NO_2$) solution (with a pH between 6.8-7.1) which is a suitable precursor in the manufacture of certain polymers.

The advantage of using ammonium acrylate produced from an acrylic acid obtained from the biocatalytic process herein described is that the acrylic acid is relatively free of undesired by-products, as the acrylonitrile substrate has been converted to acrylic acid in a single enzymatically catalysed step, without any unwanted side-reactions.

What is claimed:

1. A strain of *Rhodococcus rhodochrous* having been deposited under NCIMB Accession Number 42803.

2. The strain of claim 1, wherein the strain expresses a nitrilase enzyme which is capable of catalyzing the conversion of acrylonitrile to acrylic acid at concentrations of acrylonitrile exceeding 175 mM.

3. The strain of claim 1, wherein the strain is cultivated in the presence of isobutyronitrile to inhibit nitrile hydratase activity.

4. The strain of claim 1, wherein the strain is cultivated in the presence of ε-caprolactam to induce production of nitrilase.

5. A method for converting acrylonitrile to acrylic acid, the method comprising:
    (a) cultivating a strain of *Rhodococcus rhodochrous* having been deposited under NCIMB Accession Number 42803 in a growth medium containing ε-caprolactam and isobutyronitrile;
    (b) adding acrylonitrile; and
    (c) converting acrylonitrile to acrylic acid;
    wherein the conversion of acrylonitrile to acrylic acid is catalyzed by nitrilase produced by the *Rhodococcus rhodochrous* strain.

6. The method of claim 5, wherein the concentration of acrylonitrile exceeds 175 mM.

7. The method of claim 5, wherein the ε-caprolactam induces production of nitrilase.

8. The method of claim 5, wherein the isobutyronitrile inhibits nitrile hydratase activity.

* * * * *